(12) United States Patent
Nagai

(10) Patent No.: US 6,208,710 B1
(45) Date of Patent: Mar. 27, 2001

(54) X-RAY DIAGNOSTIC APPARATUS AND RADIATION DIAGNOSTIC APPARATUS

(75) Inventor: Seiichiro Nagai, Otawara (JP)

(73) Assignee: Kabushiki Kaisha Toshiba, Kawasaki (JP)

( * ) Notice: Subject to any disclaimer, the term of this patent is extended or adjusted under 35 U.S.C. 154(b) by 0 days.

(21) Appl. No.: 09/357,653

(22) Filed: Jul. 20, 1999

(30) Foreign Application Priority Data

Jul. 21, 1998 (JP) .................................................. 10-205489

(51) Int. Cl.$^7$ ...................................................... H05G 1/44
(52) U.S. Cl. ............................ 378/108; 378/97; 378/98.7
(58) Field of Search ............................... 378/62, 98, 98.2, 378/98.7, 98.8, 205, 108, 95, 97

(56) References Cited

U.S. PATENT DOCUMENTS

| | | | |
|---|---|---|---|
| 5,937,027 | * | 8/1999 | Thevenin et al. .................... 378/98.8 |
| 5,949,848 | * | 9/1999 | Gilblom .............................. 378/98.8 |
| 6,047,042 | * | 4/2000 | Khutoryansky et al. ............... 378/62 |
| 6,106,152 | * | 8/2000 | Thumberg ........................... 378/205 |

FOREIGN PATENT DOCUMENTS

| | | |
|---|---|---|
| 7-201490 | 8/1995 | (JP) . |
| 2500895 | 3/1996 | (JP) . |
| 11-9581 | 1/1999 | (JP) . |

* cited by examiner

*Primary Examiner*—David P. Porta
(74) *Attorney, Agent, or Firm*—Oblon, Spivak, McClelland, Maier & Neustadt, P.C.

(57) ABSTRACT

An X-ray diagnostic apparatus forms image data using an arbitrary region in the detectable area of a planar detector having a plurality of X-ray detector elements arrayed in a matrix. An X-ray sensor array for exposure-controlling having a plurality of X-ray sensors arrayed in a matrix overlaps the planar detector. An X-ray controller controls an X-ray tube unit on the basis of an output from the X-ray sensor array in order to optimize the X-ray dose on a subject. A controller selects at least one X-ray sensor in accordance with the position of a partial region where an image is formed. The controller controls at least one of the X-ray sensor array and X-ray controller so as to control the X-ray dose on the basis of an output from the selected X-ray sensor.

22 Claims, 11 Drawing Sheets

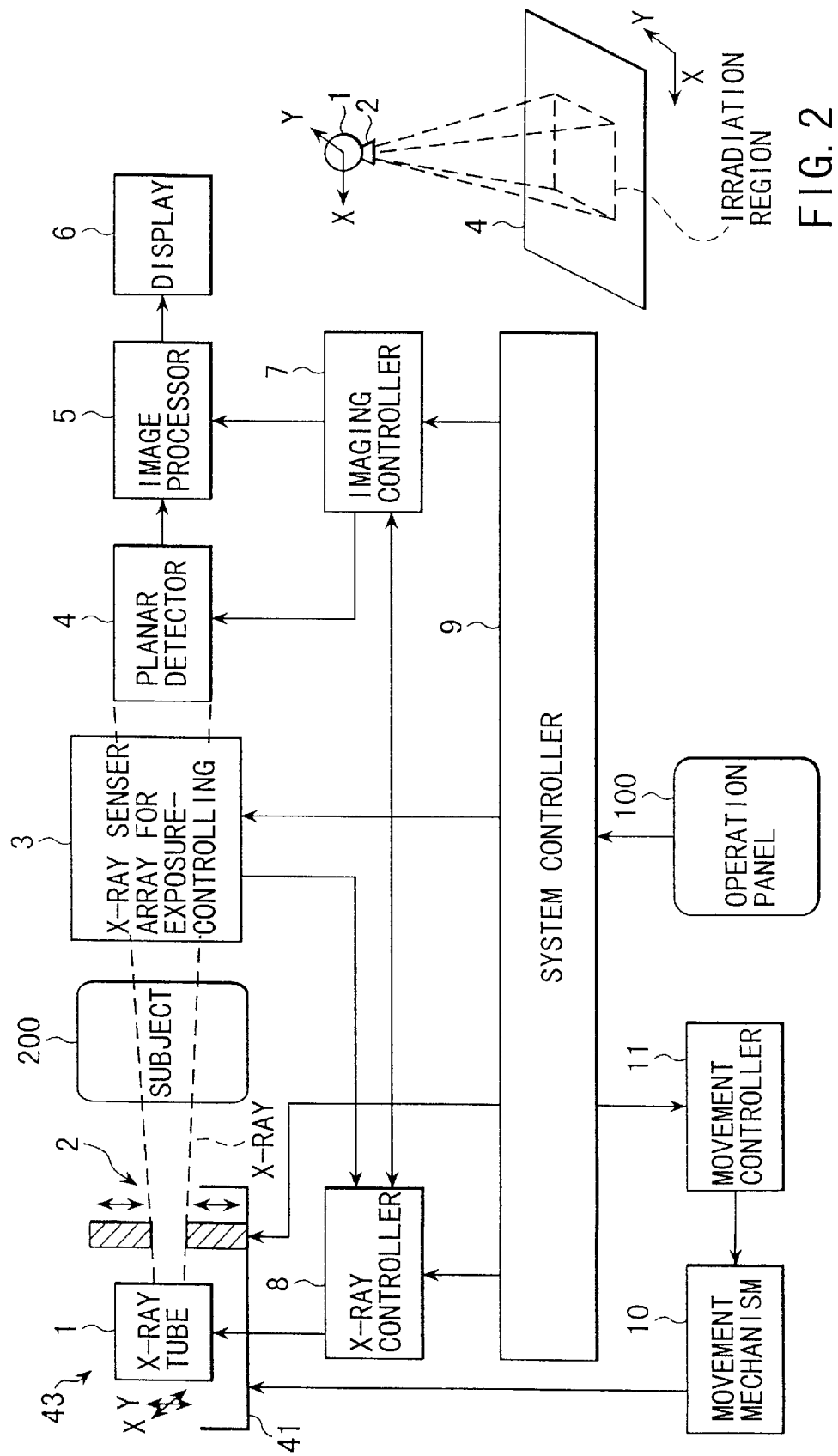

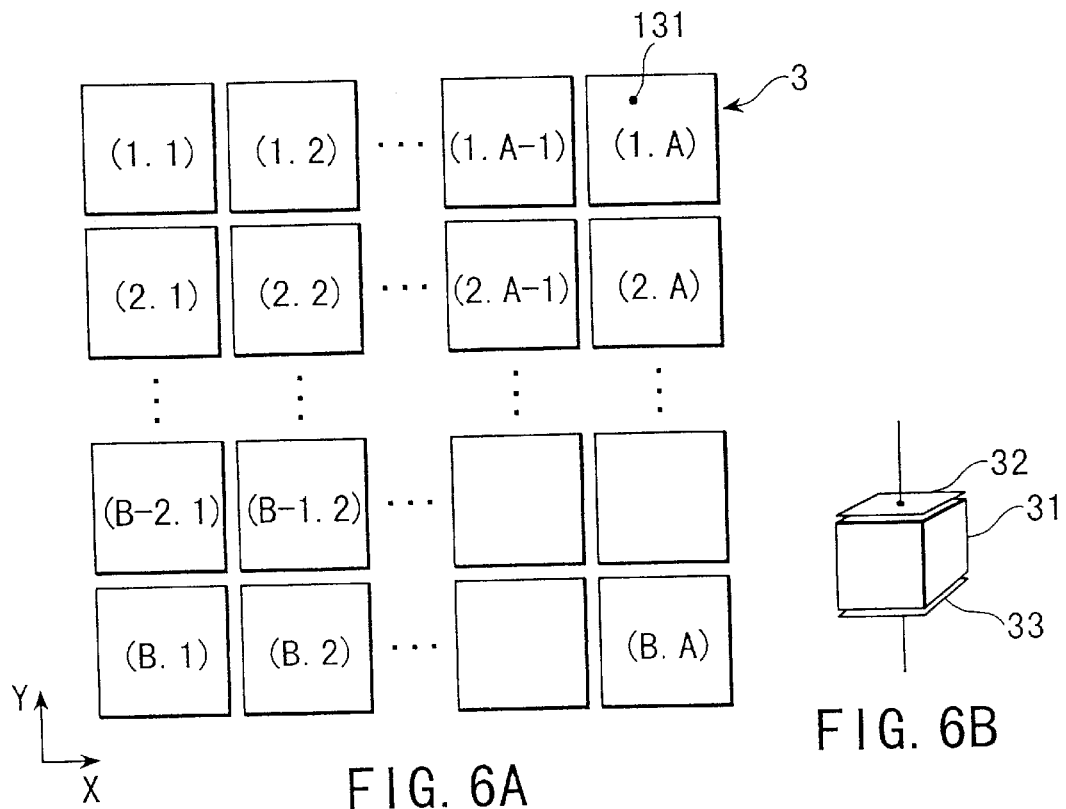
FIG. 6A
FIG. 6B
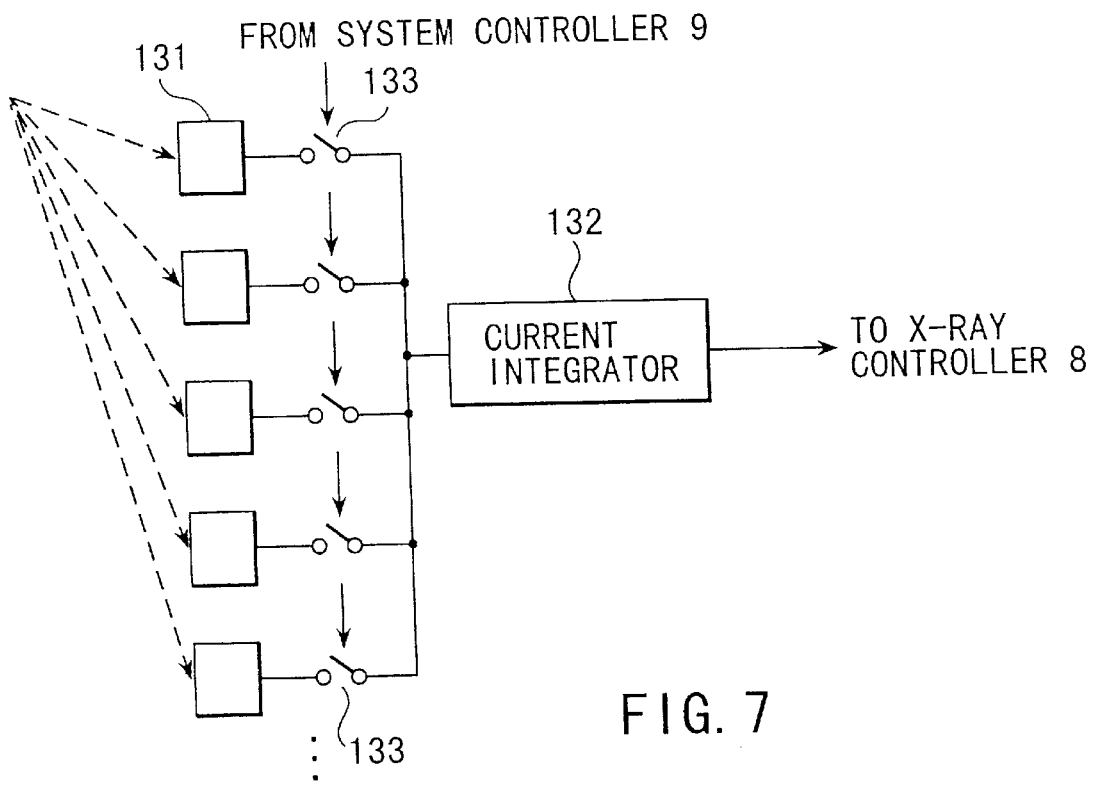
FIG. 7

X-RAY DIAGNOSTIC APPARATUS AND RADIATION DIAGNOSTIC APPARATUS

BACKGROUND OF THE INVENTION

The present invention relates to an X-ray diagnostic apparatus and radiation diagnostic apparatus for sensing an X-ray image (radiation image) of a subject.

Most of X-ray diagnostic apparatuses have an automatic exposure control function of automatically controlling the photographing time in order to keep the image density constant. The automatic exposure control is based on the following principle. An X-ray sensor is interposed between a subject and X-ray detector. An output from the X-ray sensor is temporally integrated by an integrator. The integrated value corresponds to an image density. The integrated value is compared with a reference value. When the integrated value reaches the reference value, irradiation of X-rays on the subject stops. Instead of the X-ray sensor, part of output light from an image intensifier is drawn in a photomultiplier to monitor the exposure time based on the output, or the exposure time is monitored based on part of an image signal photographed by a TV camera. Also, exposure is controlled based on an output from a planar detector prepared by arraying a plurality of semiconductor elements (Jpn. Pat. Appln. KOKAI Publication No. H7-201490). An X-ray diagnostic apparatus of this type can more appropriately control exposure, does not require any sensor other than the planar detector, and can realize cost reduction and high reliability.

In recent years, there is proposed a technique of forming a 1-frame image using not the entire detectable area of the planer detector but an arbitrary partial region (imaging region) in the detectable area (Japanese Patent Application No. H9-164249).

Since the imaging region can be arbitrarily set, as described above, the X-ray sensor for exposure-controlling may deviate from the imaging region to generate an exposure control error.

If the imaging region is set at particularly the periphery of the detectable area, X-rays are obliquely incident on the imaging region to distort an image.

BRIEF SUMMARY OF THE INVENTION

It is an object of the present invention to eliminate any exposure control error in an X-ray diagnostic apparatus and radiation diagnostic apparatus capable of forming an image using an arbitrary partial region in the detectable area.

It is another object of the present invention to eliminate any image distortion in an X-ray diagnostic apparatus and radiation diagnostic apparatus capable of forming an image using an arbitrary partial region in the detectable area.

The X-ray diagnostic apparatus according to the present invention forms image data using an arbitrary region in the detectable area of a planar detector having a plurality of X-ray detector elements arrayed in a matrix. An X-ray sensor array for exposure-controlling having a plurality of X-ray sensors arrayed in a matrix overlaps the planar detector. An X-ray controller controls an X-ray tube unit on the basis of an output from the X-ray sensor array in order to optimize the X-ray dose on a subject. A controller selects at least one X-ray sensor in accordance with the position of a partial region where an image is formed. The controller controls at least one of the X-ray sensor array and X-ray controller so as to control the X-ray dose on the basis of an output from the selected X-ray sensor. Since the X-ray dose is adjusted based on an output from an X-ray sensor corresponding to the position of a partial region where an image is formed, any exposure control error can be eliminated.

The X-ray diagnostic apparatus according to the present invention forms image data using an arbitrary region in the detectable area of a planar detector having a plurality of X-ray detector elements arrayed in a matrix. The relative positions of the planar detector and X-ray tube unit can be changed by a movement mechanism. The controller can change the relative positions in accordance with a region where an image is formed. Hence, even if the region where an image is formed is set at the periphery of the detectable area, X-rays can be substantially vertically incident on the region where an image is formed, thereby eliminating any image distortion.

Additional objects and advantages of the invention will be set forth in the description which follows, and in part will be obvious from the description, or may be learned by practice of the invention. The objects and advantages of the invention may be realized and obtained by means of the instrumentalities and combinations particularly pointed out hereinafter.

BRIEF DESCRIPTION OF THE SEVERAL VIEWS OF THE DRAWING

The accompanying drawings, which are incorporated in and constitute a part of the specification, illustrate presently preferred embodiments of the invention, and together with the general description given above and the detailed description of the preferred embodiments given below, serve to explain the principles of the invention.

FIG. 1 is a block diagram showing the arrangement of an X-ray diagnostic apparatus according to a preferred embodiment of the present invention;

FIG. 2 is a view showing an X-ray irradiation region limited by a collimator in FIG. 1;

FIG. 6A is a schematic plan view showing an X-ray sensor array for exposure-controlling in FIG. 1;

FIG. 6B is a schematic view showing the structure of each X-ray sensor in FIG. 6A;

FIG. 7 is a block diagram showing a selector and current integrator included in the X-ray sensor array for exposure-controlling in FIG. 1;

DETAILED DESCRIPTION OF THE INVENTION

Figure 3A:
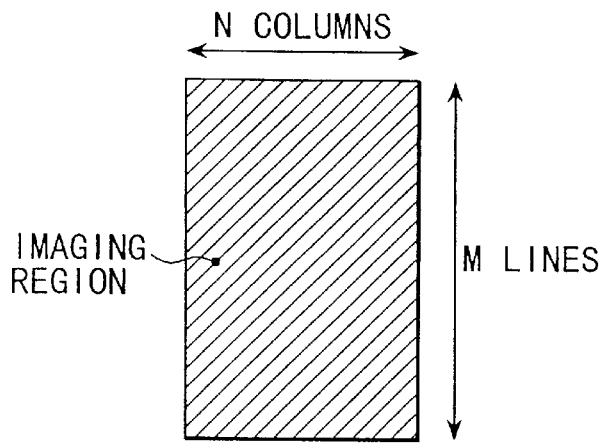
FIGS. 3A to 3F are plan views showing various imaging regions set in the detectable area of a planar detector in FIG. 1.
Figure 3B:
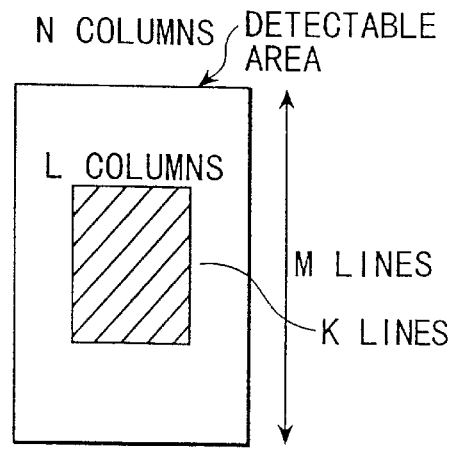
Figure 3C:
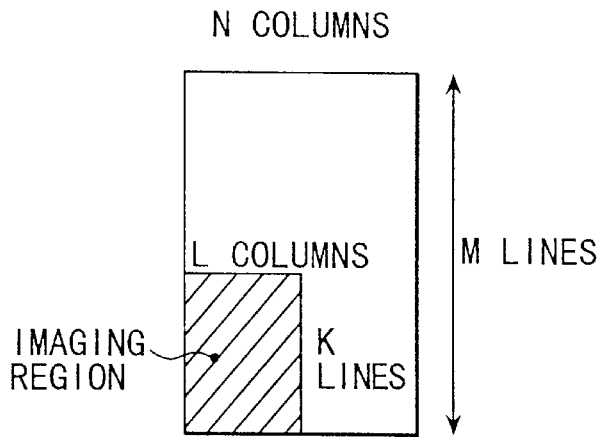
Figure 3D:
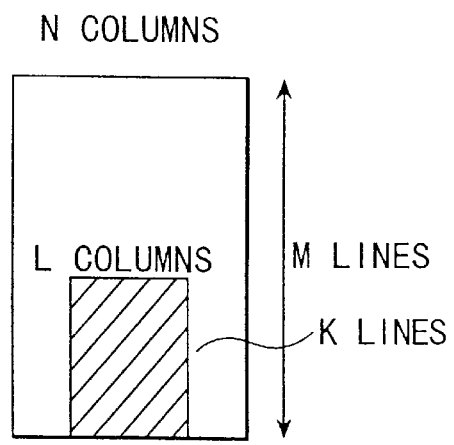
Figure 3E:
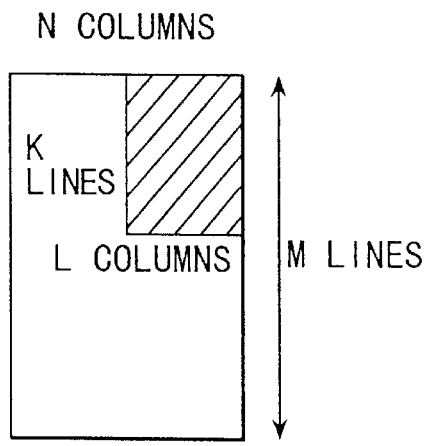
Figure 3F:
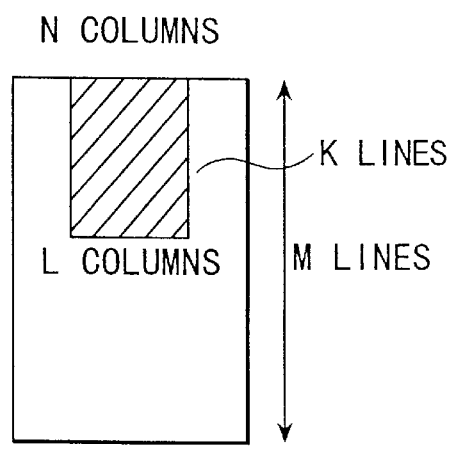
Figure 4A:
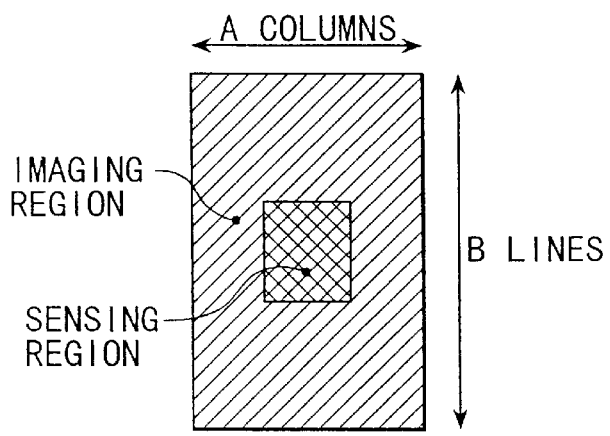
FIGS. 4A to 4F are plan views showing the sensing regions of X-ray sensors selected in accordance with the imaging regions in FIGS. 3A to 3F.
Figure 4B:
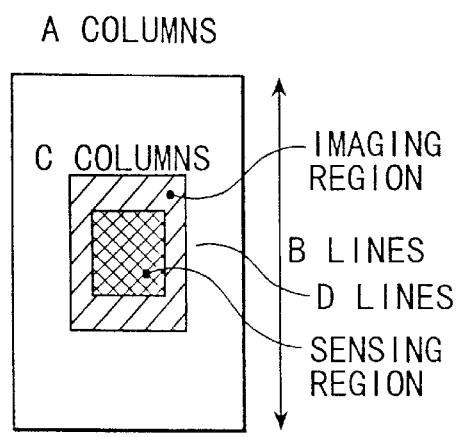
Figure 4C:
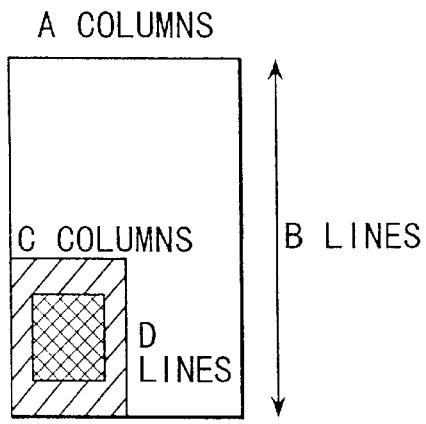
Figure 4D:
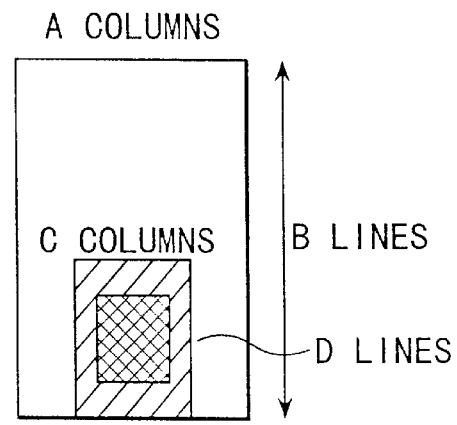
Figure 4E:
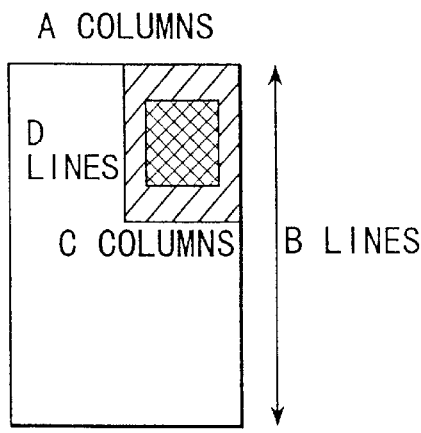
Figure 4F:
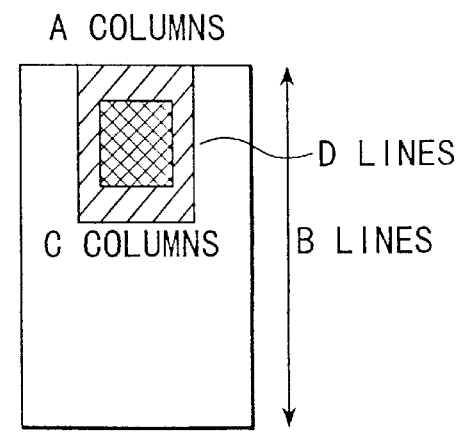

A preferred embodiment of an X-ray diagnostic apparatus and radiation diagnostic apparatus according to the present invention will be described below with reference to the several views of the accompanying drawing. FIG. 1 shows the arrangement of the X-ray diagnostic apparatus according to this embodiment. An X-ray tube unit 43 comprises an X-ray tube 1 for generating X-rays, and an X-ray collimator (to be also referred to as an X-ray stop unit) 2 for limiting the X-ray irradiation field, as shown in FIG. 2. An X-ray sensor array 3 for exposure-controlling and an imaging planar detector 4 are opposite to the X-ray tube unit 43 via a subject 200.

The detectable area of the X-ray sensor array 3 has almost the same area as the detectable area of the planar detector 4, and the X-ray sensor array 3 overlaps the front surface (X-ray incident surface) or rear surface of the planar detector 4. In this embodiment, the X-ray sensor array 3 overlaps the front surface of the planar detector 4. In this case, X-rays having transmitted through the subject pass through the X-ray sensor array 3 and are detected by the planar detector 4.

This embodiment can form not only image data corresponding to the entire detectable area of the planar detector 4, as shown in FIG. 3A, but also image data limited to an arbitrary partial region (imaging region) in the detectable area, as shown in FIGS. 3B to 3F. An operator inputs a user instruction via an operation panel 100 in order to arbitrarily set the position, shape, and size of the imaging region.

Image data corresponding to a set imaging region is formed under the control of an imaging controller 7 to the planar detector 4 and image processor 5. Under this control, the planar detector 4 outputs a signal in the imaging region, and the image processor 5 forms image data corresponding to the imaging region on the basis of this output. Note that the image processor 5 has a function of correcting image data in addition to the function of forming image data in accordance with the imaging region. This correction will be described later. The corrected image data is sent to a display 6. The display 6 displays an X-ray density image based on the image data.

An X-ray controller 8 applies a high voltage to the X-ray tube 1 in order to generate X-rays from the X-ray tube 1. The X-ray controller 8 has an exposure control function of adjusting the X-ray dose by stopping generation of X-rays or decreasing the X-ray intensity on the basis of an output from the X-ray sensor array 3 so as to attain a desired image density.

The X-ray sensor array 3 has a plurality of X-ray sensors arrayed in a matrix, as will be described below. As shown in FIGS. 4A to 4F, of these X-ray sensors, at least one X-ray sensor corresponding to the range of the imaging region, more particularly, an X-ray sensor closest to the center of the imaging region is selected by a system controller 9 for exposure control. Then, at least some of X-rays incident on the imaging region of the planar detector 4 are incident on the selected X-ray sensor.

The X-ray collimator 2 has a plurality of assembled movable lead plates. These movable lead plates move under the control of the system controller 9 so as to make the X-ray irradiation field coincide with the imaging region set on the detectable area of the planar detector 4. This prevents unwanted X-rays from irradiating the subject 200.

The X-ray tube 1 and X-ray collimator 2 are mounted on a common base 41, and their positions are fixed. The common base 41 is moved by a movement mechanism 10 controlled by a movement controller 11 so as to make X-rays from the X-ray tube 1 substantially vertically strike the center of the imaging region set on the detectable area of the planar detector 4.

Figures 5A, 5B:
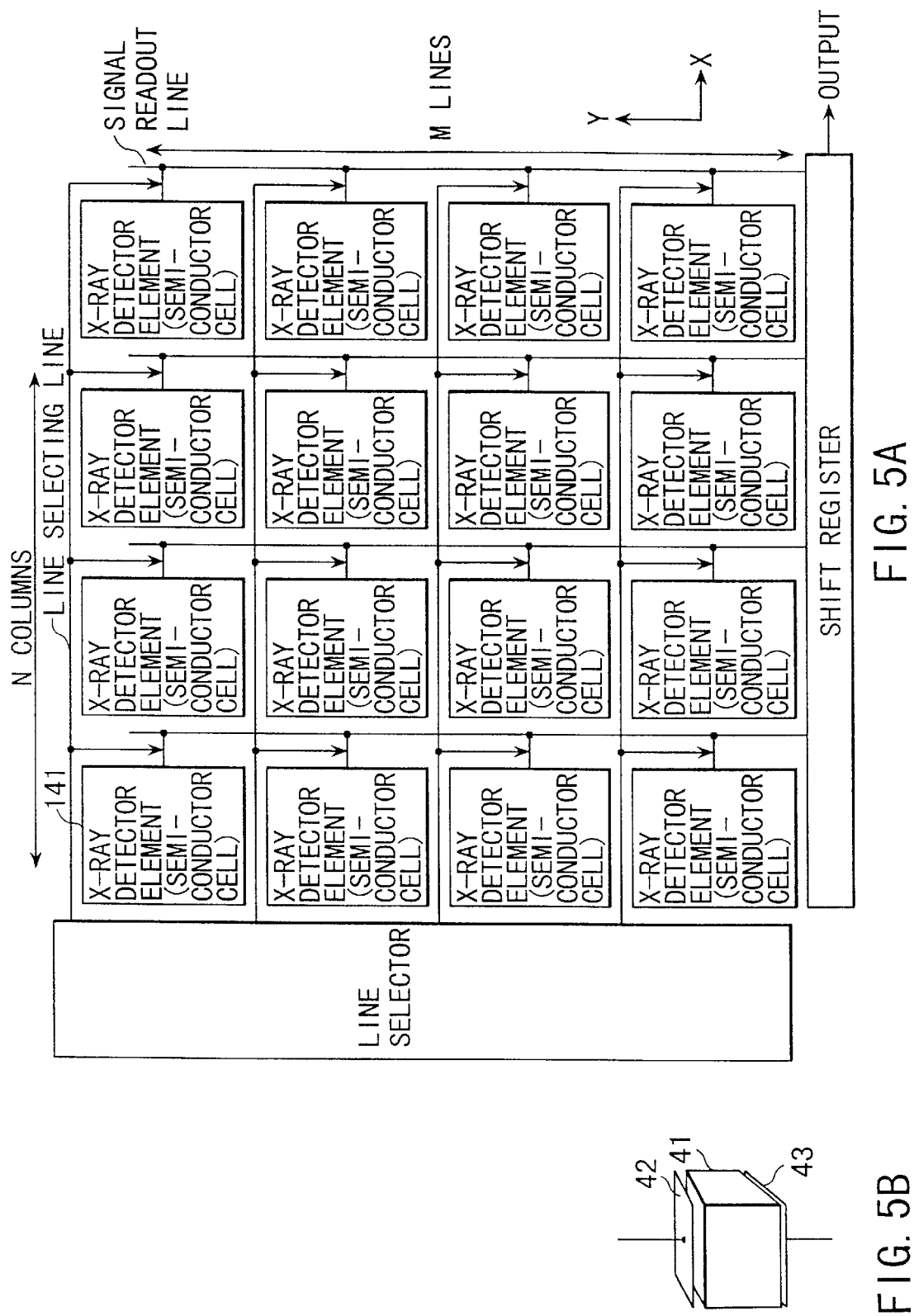
FIG. 5A is a schematic plan view showing the planar detector in FIG. 1.
FIG. 5B is a schematic view showing the structure of each X-ray detector element in FIG. 5A.

As shown in FIG. 5A, the planar detector 4 has a plurality of X-ray detector elements 141 arrayed in a matrix. As shown in FIG. 5B, each X-ray detector element 141 adopts a semiconductor cell formed from a semiconductor layer 41, a voltage application electrode 42 formed on the upper surface of the semiconductor layer 41, and a signal electrode 43 formed on the lower surface of the semiconductor layer 41. When X-rays are incident on the semiconductor layer 41, electron-hole pairs are produced by ionization. The electrons and holes are respectively attracted to the reverse-biased electrodes 42 and 43. As a result, a signal current corresponding to the incident X-ray intensity is generated.

As shown in FIG. 6A, the X-ray sensor array 3 has a plurality of X-ray sensors 131 arrayed in a matrix. As shown in FIG. 6B, similar to the X-ray detector element 141 of the planar detector 4, each X-ray sensor 131 is formed from a semiconductor layer 31, a voltage application electrode 32 formed on the upper surface of the semiconductor layer 31, and a signal electrode 33 formed on the lower surface of the semiconductor layer 31.

As shown in FIG. 7, the X-ray sensor array 3 comprises a plurality of selector switches 133 respectively corresponding to the plurality of sensors 131, and a current integrator 132 for integrating a signal current output from a sensor 131 selected by the selector switches 133. These selector switches 133 are independently ON/OFF-controlled by the system controller 9. This switching control selects at least one X-ray sensor 131 corresponding to the position of the imaging region.

Figure 8:
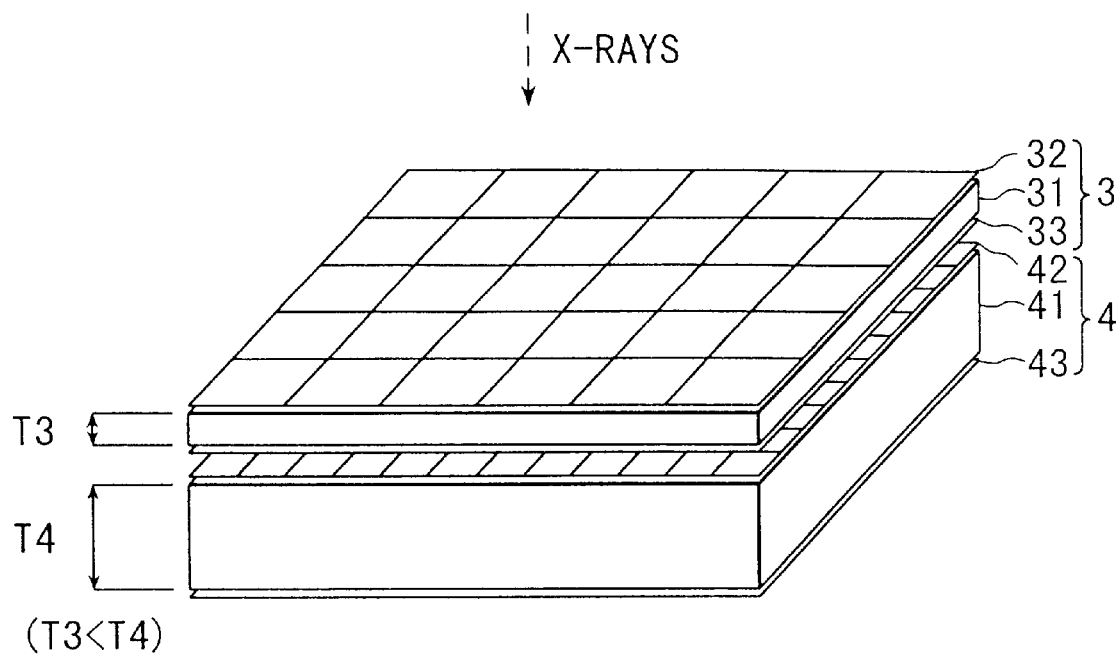
FIG. 8 is a perspective view showing the planar detector and X-ray sensor array for exposure-controlling in FIG. 1.

As shown in FIG. 8, the semiconductor layer 31 of the X-ray sensor 131 is formed thinner than the semiconductor layer 41 of the planar detector 4 in order to reduce the X-ray absorption amount and ensure a certain transmission X-ray amount. To the contrary, the semiconductor layer 41 of the planar detector 4 is formed thicker than the semiconductor layer 31 of the X-ray sensor 131 in order to increase the X-ray absorption amount and increase the X-ray conversion efficiency. Note that each X-ray detector element 141 may be formed from a scintillator layer for converting incident X-rays into light, and a photodiode for converting the light into an electrical signal. Similarly, each X-ray sensor 131 may be formed from a scintillator layer for converting incident X-rays into light, and a photodiode for converting the light into an electrical signal. In this case, the scintillator layer of the X-ray detector element 141 is formed thicker than the scintillator layer of the X-ray sensor 131.

Figure 9:
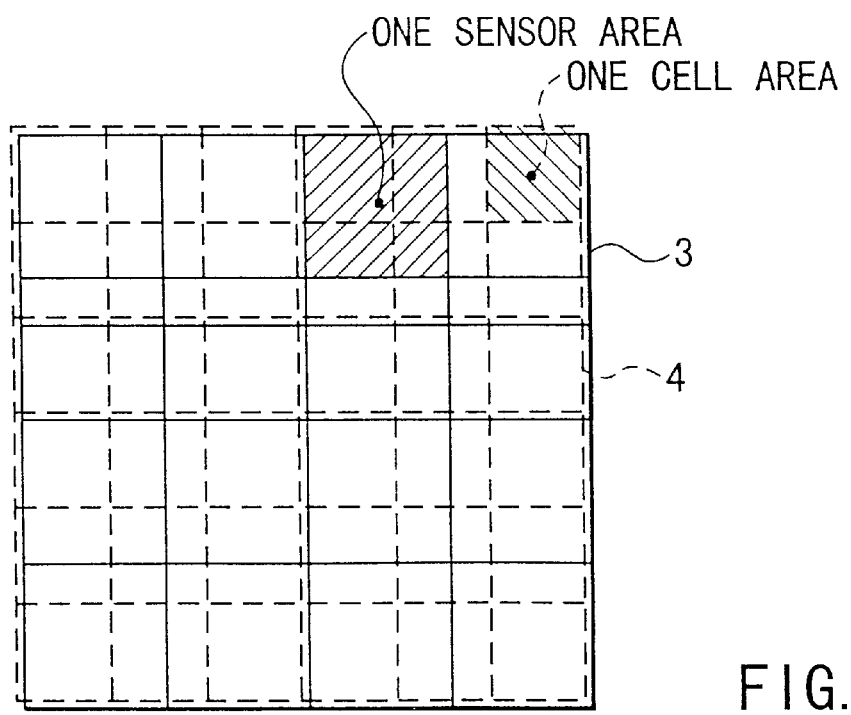
FIG. 9 is a schematic plan view showing the planar detector and X-ray sensor array for exposure-controlling in FIG. 1.

As shown in FIG. 9, the X-ray sensor array 3 is lower in spatial resolution than the planar detector 4 for the purpose of cost reduction and the like. That is, the X-ray sensors 131 of the X-ray sensor array 3 are discretely sparsely arrayed, whereas the X-ray detector elements 141 of the planar detector 4 are densely arrayed to increase the spatial resolution of the image.

Figure 10A:
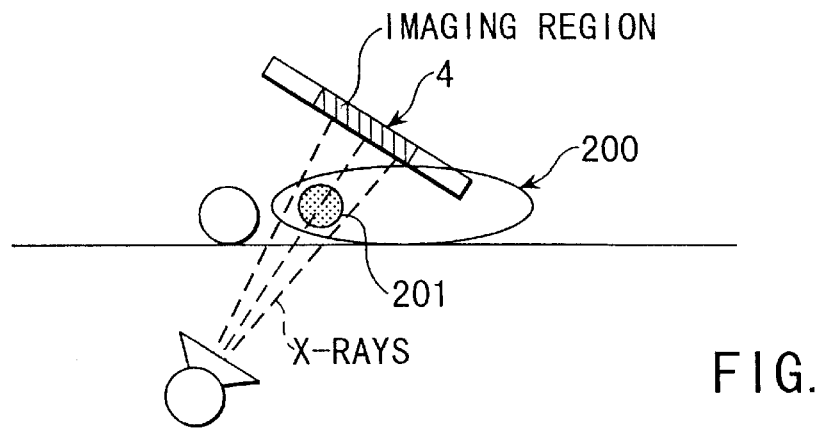
FIG. 10A is a view showing the posture of the planar detector in oblique angiocardiography of a heart in this embodiment.
Figure 10B:
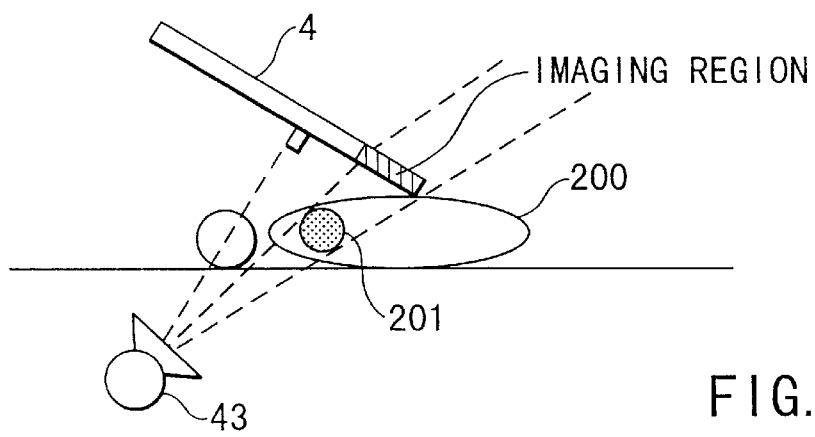
FIG. 10B is a view showing the imaging region in the detectable area of the planar detector in oblique angiocardiography of a heart in this embodiment.
Figure 10C:
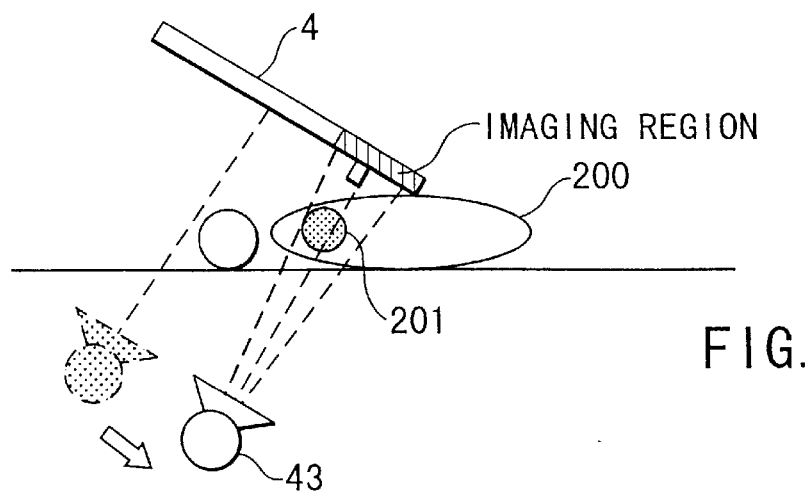
FIG. 10C is a view showing the position of an X-ray tube unit in oblique angiocardiography of a heart in this embodiment.

Operation of this embodiment will be explained. Assume oblique angiocardiography of a heart. As shown in FIG. 10A, the edge of the planar detector 4 may touch the chest of the subject 200 to obstruct angio-cardiography. To avoid this, the imaging region is set at the periphery of the detectable area, as shown in FIG. 10B. In this case, X-rays are obliquely incident on the imaging region to distort an image. In this embodiment, as shown in FIG. 10C, the movement mechanism 10 controlled by the movement controller 11 moves the X-ray tube unit 43 to immediately above the set imaging region. That is, the X-ray tube unit 43 moves such that the X-rays from the X-ray tube 1 substantially vertically strike the center of the set imaging region. Consequently, almost all image distortions can be eliminated.

Then, as shown in FIGS. 4A to 4F, the system controller 9 selects an X-ray sensor 131 closest to the center of the set imaging region among the plurality of X-ray sensors 131 constituting the X-ray sensor array 3.

A plurality of movable lead plates constituting the X-ray collimator 2 move under the control of the system controller 9 so as to make the X-ray irradiation field coincide with the set imaging region. Accordingly, unwanted exposure can be avoided.

Upon completion of the above preparation, the X-ray tube 1 starts generating X-rays. The X-rays pass through the X-ray collimator 2, subject 200, and sensor array 3 to reach the planar detector 4. The image processor 5 forms image data corresponding to the imaging region on the basis of an output from the planar detector 4. The image processor 5 further corrects the image data. The display 6 displays a fluoroscopic image or still image based on the corrected image data.

While X-rays are generated, the X-ray controller 8 monitors the X-ray dose on the basis of an output from the selected X-ray sensor 131. When the integrated value of the output from the X-ray sensor 131 exceeds the threshold, the X-ray controller 8 stops generating the X-rays or decreases the X-ray intensity, thereby optimizing the image density.

Since the X-ray sensor array 3 is arranged in front of the planar detector 4, as described above, the X-ray shadow of the X-ray sensor array 3 is projected on the detectable area of the planar detector 4. The image processor 5 performs correction of removing this X-ray shadow from image data. The image processor 5 also performs correction of removing the offset component of the X-ray detector element of the planar detector 4.

Figure 11A:
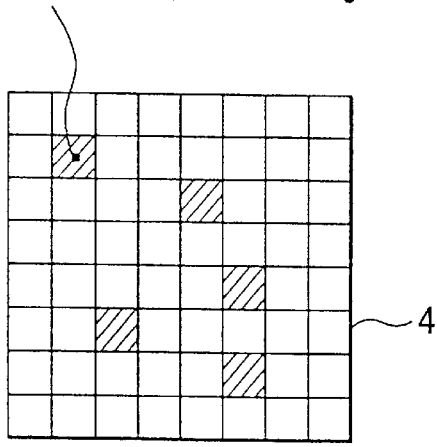
FIG. 11A is a schematic view showing the offset component distribution of the planar detector in FIG. 1.
Figure 11B:
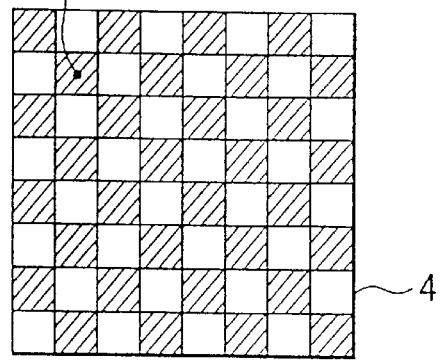
FIG. 11B is a schematic view showing the X-ray shadow of the X-ray sensor array that is projected on the detectable area of the planar detector in FIG. 1.

FIG. 11A shows a signal SIG1 output from the X-ray detector element 141 of the planar detector 4 when no X-rays are generated. A value "a" of the signal SIG1 is a offset component. The offset component "a" is measured in advance for each X-ray detector element 141, and the data is supplied to the image processor 5 in advance. FIG. 11B shows a signal SIG2 output from the X-ray detector element 141 of the planar detector 4 when X-rays are generated while no subject 200 is interposed between the X-ray tube unit 43, and the X-ray sensor array 3 and planar detector 4. Letting IXeven be the X-ray intensity, the signal SIG2 is given by $$SIG2 = k \cdot IXeven + a$$

where k is an error parameter arising from the X-ray shadow and sensitivity, and can be calculated from the known SIG2, IXeven, and a. The parameter k is measured in advance for each X-ray detector element 141, and the data is supplied to the image processor 5 in advance.

Figure 11C:
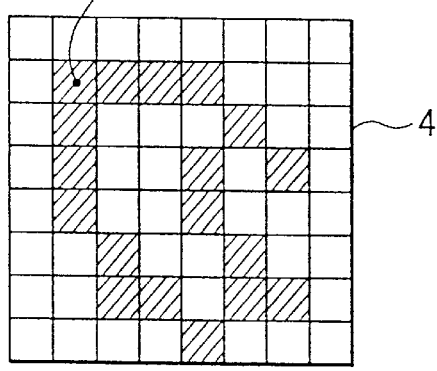
FIG. 11C is a view showing an output signal from a given X-ray detector element of the planar detector in FIG. 1 in actual photographing.
Figure 11D:
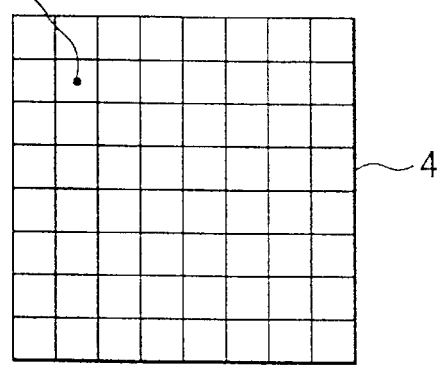
FIG. 11D is a view showing the principle of signal correction in a processor in FIG. 1.

FIG. 11C shows an output signal SIG3 from the X-ray detector element 141 of the planar detector 4 when the subject 200 is actually photographed while being interposed between the X-ray tube unit 43, and the X-ray sensor array 3 and planar detector 4. Letting IX be a transmission X-ray intensity attenuated by the subject 200 or the like, the signal SIG3 is given by $$SIG3 = k \cdot IX + a$$

As shown in FIG. 1D, therefore, the transmission X-ray intensity IX is calculated by $$IX = (SIG3 - a)/k$$

The offset component can be removed from the transmission X-ray intensity IX or derived value to obtain image data free from the influence of any X-ray shadow.

Figure 12:
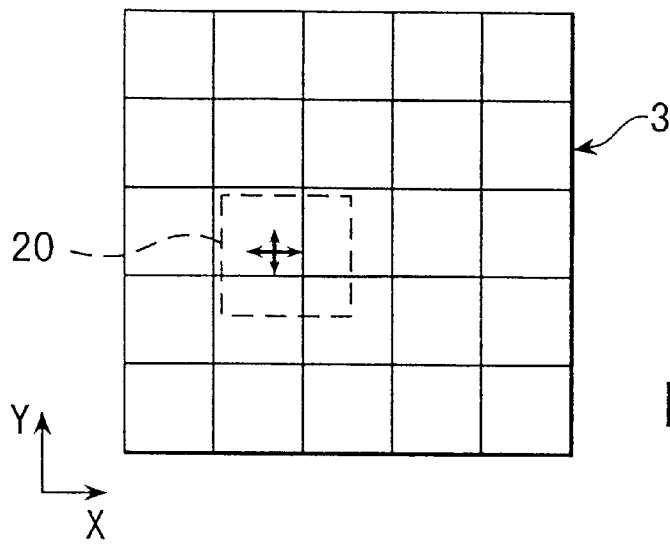
FIG. 12 is a view showing a movable sensor which can replace the X-ray sensor array in FIG. 1.

Note that the same effects can be attained by providing at least one vertically movable X-ray sensor 20, as shown in FIG. 12, in place of selecting at least one X-ray sensor 131 in accordance with the position of the imaging region.

Figure 13:
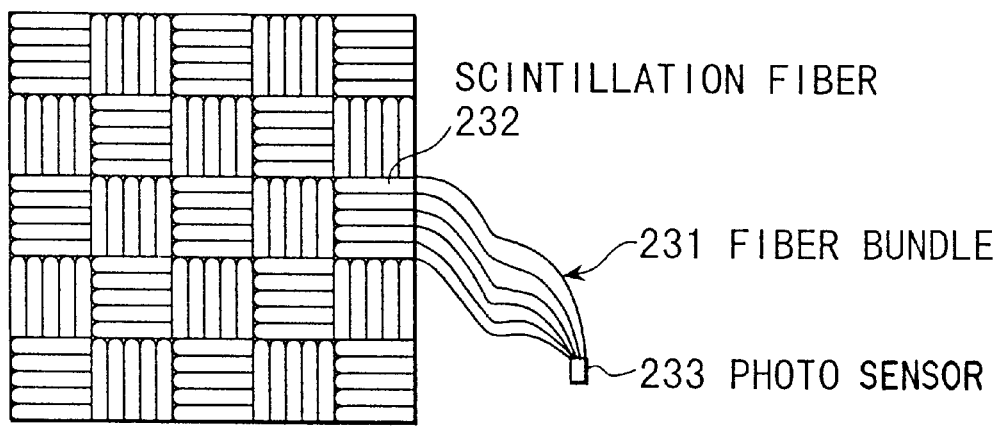
FIG. 13 is a view showing a scintillation fiber sensor which can replace the X-ray sensor array in FIG. 1.
Figure 14:
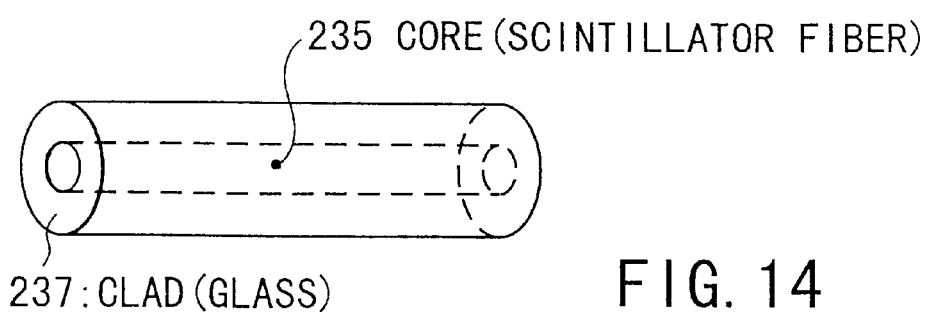
FIG. 14 is a view showing the internal structure of the scintillator fiber in FIG. 13.

In the above description, the semiconductor element is adopted as the X-ray detector element 141. Alternatively, as shown in FIG. 13, the X-ray detector element 141 may be formed from a bundle 231 of a plurality of scintillation fibers 232. As shown in FIG. 14, each scintillation fiber 232 is made up of the core of a scintillator fiber 235 and a glass clad 237. Light generated in the scintillator fiber 235 by incident X-rays passes through the glass clad 237 and is detected by a photo sensor 233.

Figure 15:
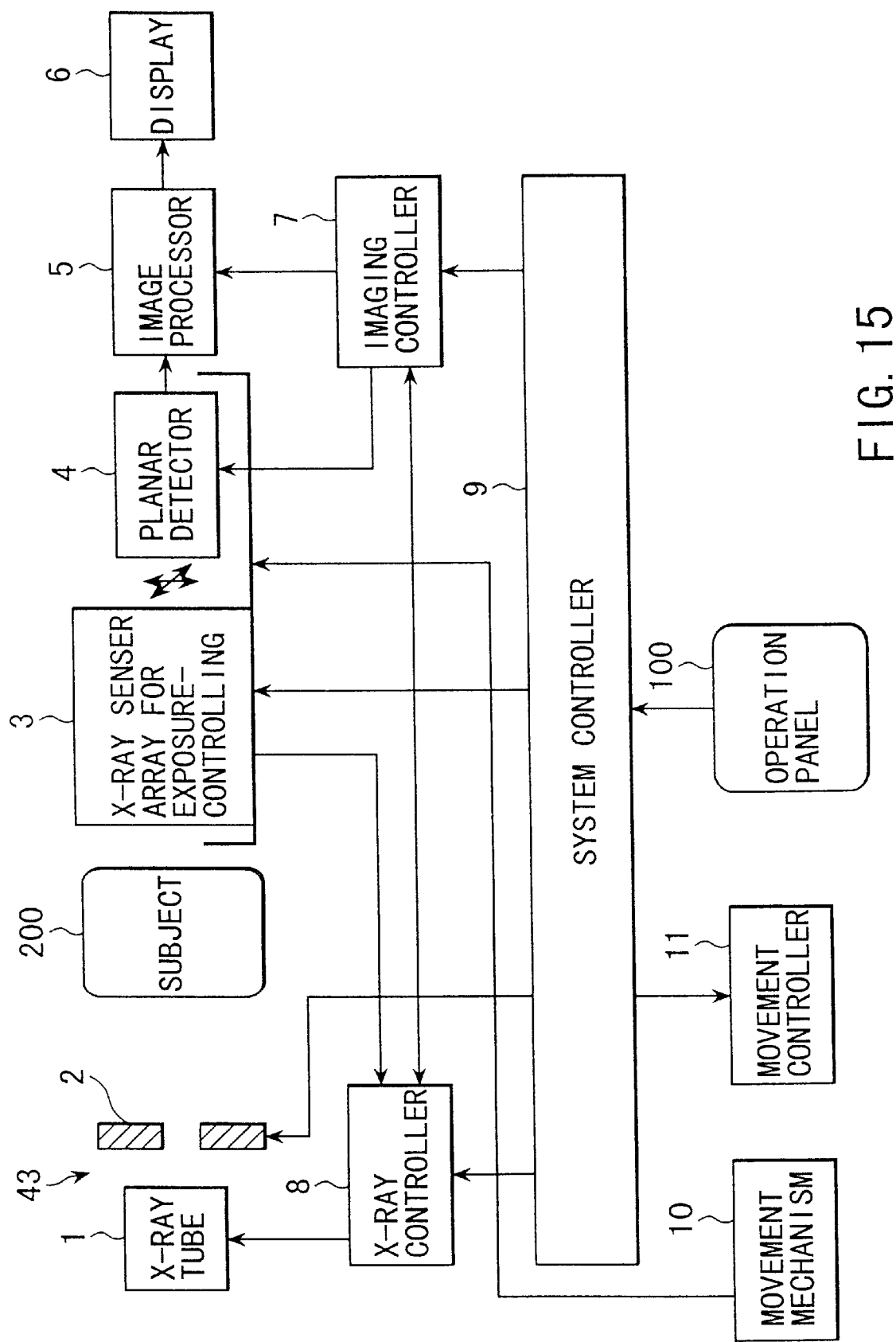
FIG. 15 is a block diagram showing the arrangement of an X-ray diagnostic apparatus in which the X-ray sensor array and planar detector are movable instead of the X-ray tube unit in this embodiment.

In the above description, the X-ray tube unit 43 moves. Alternatively, as shown in FIG. 15, the X-ray tube unit 43 may be fixed, and the X-ray sensor array 3 and planar detector 4 may move instead.

Figure 16:
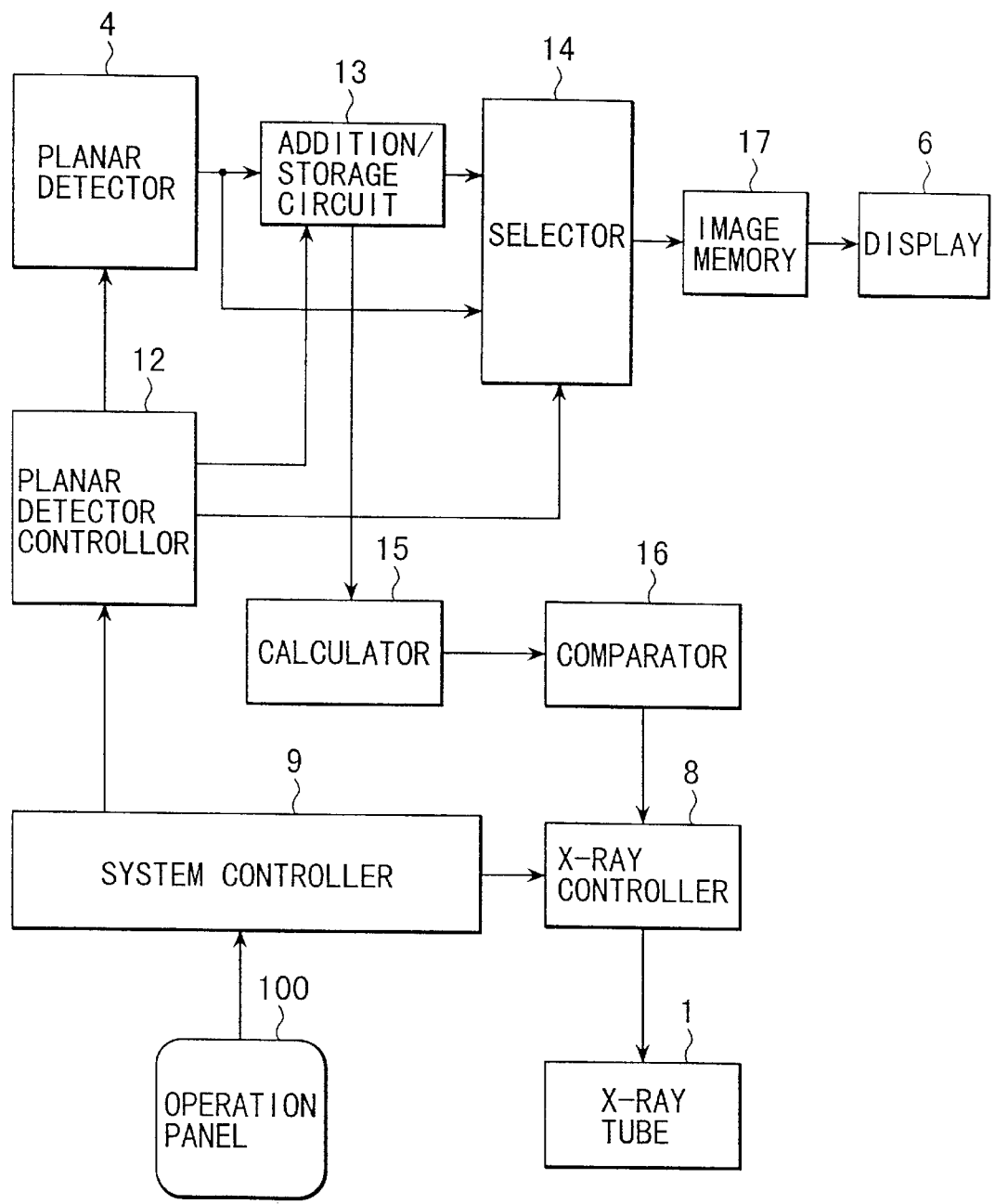
FIG. 16 is a block diagram showing the arrangement of an X-ray diagnostic apparatus in which exposure is controlled based on an output from the planar detector in this embodiment.

In the above description, the X-ray sensor array 3 is arranged, and exposure is controlled based on an output from the X-ray sensor array 3. Alternatively, as shown in FIG. 16, the X-ray sensor array 3 may be removed, and exposure may be controlled based on an output from the planar detector 4. outputs from a few X-ray detector elements 141 selected in accordance with the imaging region are independently temporarily added and stored by an addition/storage circuit 13. The sums of the few X-ray detector elements 141 are summed up by a calculator 15. The total value is compared with the threshold by a comparator 16. When the total value exceeds the threshold, the X-ray controller 8 stops generating X-rays or decreases the X-ray intensity.

Additional advantages and modifications will readily occur to those skilled in the art. Therefore, the invention in its broader aspects is not limited to the specific details and representative embodiments shown and described herein. Accordingly, various modifications may be made without departing from the spirit or scope of the general inventive concept as defined by the appended claims and their equivalents.

What is claimed is:

1. An X-ray diagnostic apparatus comprising:
   an X-ray tube unit for irradiating a subject with X-rays;
   a planar detector which is opposite to said X-ray tube unit via the subject, said planar detector having a plurality of X-ray detector elements arrayed in a matrix;
   an X-ray sensor array for exposure-controlling which overlaps said planar detector, said X-ray sensor array having a plurality of X-ray sensors arrayed in a matrix;
   a processor for forming image data on the basis of an output from said X-ray detector element;
   an X-ray controller for controlling an X-ray dose on the basis of an output from said X-ray sensor array; and
   a controller for controlling said processor so as to make the formed image data correspond to a desired partial region in a detectable area of said planar detector, said controller selecting at least one X-ray sensor among said plurality of X-ray sensors on the basis of a position of the partial region.

2. An apparatus according to claim 1, wherein said controller selects at least one X-ray sensor corresponding to a range of the partial region so as to make at least some of X-rays incident on the partial region of said planar detector be incident on said selected X-ray sensor.

3. An apparatus according to claim 1, wherein said controller selects an X-ray sensor closest to a center of the partial region.

4. An apparatus according to claim 1, wherein said X-ray sensor array comprises a selector for selectively outputting a signal of one of said plurality of X-ray sensors, and an integrator for temporarily integrating a signal current output from said selector.

5. An apparatus according to claim 1, wherein said planar detector is higher in spatial resolution than said X-ray sensor array.

6. An apparatus according to claim 1, wherein said X-ray sensors of said X-ray sensor array are discretely arrayed.

7. An apparatus according to claim 1, wherein each X-ray detector element is formed from a semiconductor layer and an electrode for outputting a signal current generated by ionization of X-rays incident on the semiconductor layer, each X-ray sensor is formed from a semiconductor layer and an electrode for outputting a signal current generated by ionization of X-rays incident on the semiconductor layer, and the semiconductor layer of said X-ray detector element is thicker than the semiconductor layer of said X-ray sensor.

8. An apparatus according to claim 1, wherein each X-ray detector element is formed from a scintillator layer for converting incident X-rays into light and a photodiode for converting the light into an electrical signal, each X-ray sensor is formed from a scintillator layer for converting incident X-rays into light and a photosensor for converting the light into an electrical signal, and the scintillator layer of said X-ray detector element is thicker than the scintillator layer of said X-ray sensor.

9. An apparatus according to claim 1, wherein each X-ray detector element is formed from a semiconductor layer and an electrode for outputting a signal current generated by ionization of X-rays incident on the semiconductor layer, each X-ray sensor is formed from a scintillator layer for converting incident X-rays into light and a photosensor for converting the light into an electrical signal.

10. An apparatus according to claim 1, wherein each X-ray detector element is formed from a scintillator layer for converting incident X-rays into light and a photosensor for converting the light into an electrical signal, each X-ray sensor is formed from a semiconductor layer and an electrode for outputting a signal current generated by ionization of X-rays incident on the semiconductor layer.

11. An apparatus according to claim 1, wherein said X-ray sensor array is interposed between the subject and said planar detector.

12. An apparatus according to claim 1, wherein said X-ray sensor array is interposed between the subject and said planar detector, and said processor has a function of correcting image data in order to effectively remove influence of an X-ray shadow of said X-ray sensor array from the image data.

13. An apparatus according to claim 1, wherein said processor has a function of correcting image data in order to effectively remove a offset component of said X-ray detector element from the image data.

14. An apparatus according to claim 1, wherein each X-ray sensor is formed from a bundle of scintillation fibers each prepared by coating a scintillator fiber core for converting incident X-rays into light with a glass clad, and a photosensor for converting output light which is converted by said scintillator fiber and guided by said clad, into a signal current.

15. An X-ray diagnostic apparatus comprising:
    an X-ray tube unit for irradiating a subject with X-rays;
    a planar detector which is opposite to said X-ray tube unit via the subject, said planar detector having a plurality of X-ray detector elements arrayed in a matrix;
    a movement mechanism for changing relative positions of said X-ray tube unit and planar detector;
    a processor for forming image data on the basis of an output from said X-ray detector element; and
    a controller for controlling said processor so as to make the formed image data correspond to a desired partial region in a detectable area of said planar detector, said controller controlling said movement mechanism in order to change the relative positions of said X-ray tube unit and planar detector in accordance with a position of the partial region.

16. An apparatus according to claim 15, wherein said controller controls to make X rays be substantially vertically incident on a center of the partial region of said planar detector.

17. An apparatus according to claim 15, further comprising a movement mechanism for moving said X-ray tube unit.

18. An apparatus according to claim 15, further comprising a movement mechanism for moving said planar detector.

19. An apparatus according to claim 15, wherein said X-ray tube unit comprises an X-ray tube and collimator, and said collimator is fixed with respect to said X-ray tube.

20. An X-ray diagnostic apparatus comprising:
    an X-ray tube unit for irradiating a subject with X-rays;
    a planar detector which is opposite to said X-ray tube unit via the subject, said planar detector having a plurality of X-ray detector elements arrayed in a matrix;
    an X-ray sensor array which overlaps said planar detector, said X-ray sensor array having a plurality of X-ray sensors arrayed in a matrix;

a movement mechanism for changing relative positions of said X-ray tube unit and planar detector;

a processor for forming image data on the basis of an output from said X-ray detector element;

an X-ray controller for controlling an X-ray dose on the basis of an output from said X-ray sensor array; and a controller for controlling said processor so as to make the formed image data correspond to a desired partial region in a detectable area of said planar detector, said controller selecting at least one X-ray sensor corresponding to a position of the partial region, and said controller controlling said movement mechanism in order to change the relative positions of said X-ray tube unit and planar detector in accordance with the position of the partial region.

21. An apparatus according to claim 20, wherein said X-ray sensor array for exposure-controlling is fixed to said planar detector.

22. A radiation diagnostic apparatus comprising:

a radiation tube unit for irradiating a subject with radiation;

a planar detector which is opposite to said radiation tube unit via the subject, said planar detector having a plurality of radiation detector elements arrayed in a matrix;

a radiation sensor array for exposure-controlling which overlaps said planar detector, said radiation sensor array having a plurality of radiation sensors arrayed in a matrix;

a movement mechanism for changing relative positions of said radiation tube unit and planar detector;

a processor for forming image data on the basis of an output from said radiation detector element;

a radiation controller for controlling a radiation dose on the basis of an output from said radiation sensor array; and a controller for controlling said processor so as to make the formed image data correspond to a desired partial region in a detectable area of said planar detector, said controller selecting at least one radiation sensor corresponding to a position of the partial region, and said controller controlling said movement mechanism in order to change the relative positions of said radiation tube unit and planar detector in accordance with the position of the partial region.

* * * * *